United States Patent [19]

Merce-Vidal et al.

[11] Patent Number: 5,536,836

[45] Date of Patent: Jul. 16, 1996

[54] PROCESS FOR THE PREPARATION OF 2-(4-[4-(4-CHLORO-1-PYRAZOLYL) BUTYL]-1-PIPERAZINYL)PYRIMIDINE (LESOPITRON)

[75] Inventors: Ramon Merce-Vidal; Jordi Frigola-Constansa, both of Barcelona, Spain

[73] Assignee: Laboratorios Del Dr. Esteve, S.A., Barcelona, Spain

[21] Appl. No.: 240,111

[22] Filed: May 9, 1994

[30] Foreign Application Priority Data

May 10, 1993 [FR] France ................... 93 05586

[51] Int. Cl.[6] .................................. C07D 401/14
[52] U.S. Cl. ................................................ 544/295
[58] Field of Search ............................... 544/295

[56] References Cited

U.S. PATENT DOCUMENTS

| | | | |
|---|---|---|---|
| 4,351,939 | 9/1982 | Simms et al. | 544/230 |
| 4,423,049 | 12/1983 | Temple, Jr. | 424/251 |
| 4,524,206 | 6/1985 | New et al. | 544/230 |
| 4,892,943 | 1/1990 | Abou-Gharbia | 540/575 |
| 5,162,323 | 11/1992 | Frigola-Constansa et al. | 514/252 |
| 5,227,486 | 7/1993 | Merce-Vidal et al. | 544/295 |

FOREIGN PATENT DOCUMENTS 0382637  8/1990  European Pat. Off. .

Primary Examiner—Mukund J. Shah
Assistant Examiner—Matthew V. Grumbling
Attorney, Agent, or Firm—Dressler, Goldsmith, Shore & Milnamow, Ltd.

[57] ABSTRACT

The present invention relates to a process for the preparation of 2-{4-[4-(4-chloro-1-pyrazolyl)butyl]-1-piperazinyl}pyrimidine (Lesopitron) of formula I:

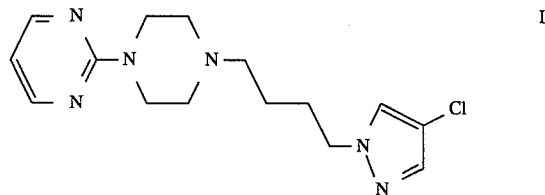

characterized in that the reaction between 2-(1-piperazinyl)pyrimidine, 4-chloropyrazole and the carbon chain of formula (III)

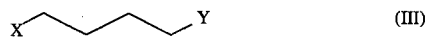

in which X and Y, which may be identical or different, represent a suitable leaving group, is carried out in a single step in a suitable solvent.

10 Claims, No Drawings

PROCESS FOR THE PREPARATION OF 2-(4-[4-(4-CHLORO-1-PYRAZOLYL) BUTYL]-1-PIPERAZINYL)PYRIMIDINE (LESOPITRON)

The present invention relates to a new process for the preparation of 2-{4-[4-(4-chloro-1-pyrazolyl)-butyl]-1-piperazinyl}pyrimidine (Lesopitron) of formula I:

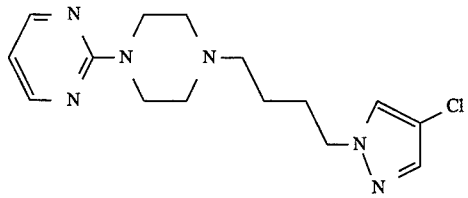

Lesopitron (E-4424) is a compound having pharmacological activity on the central nervous system, exhibiting anxiolytic and tranquillizing activity (EP-A 382,637). In addition, it may be used in the treatment of other behavioural disorders (EP-A 429,360 and EP-A 497,658).

The Applicant has described various syntheses of Lesopitron (EP-A 382,637 and EP-A 502,786). In general, these syntheses are all based on the following three fragments of the final product:

a) pyrimidinylpiperazine (II),
b) disubstituted aliphatic chain containing four carbon atoms (III), and
c) 4-chloropyrazole (IV).

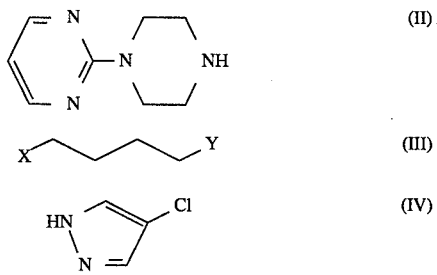

In the general formula (III), X and Y represent a leaving group such as the tosyloxy or mesyloxy groups or a halogen atom.

This type of synthesis is principally carried out in two steps:
condensation of the carbon chain (III) with one of the fragments, (II) or (IV), then
condensation of the product obtained with the second unit, (IV) or (II) respectively.

The present invention relates to a new process for the preparation of 2-{4-[4-(4-chloro-1-pyrazolyl)-butyl]-1-piperazinyl}pyrimidine (Lesopitron) (I), in which condensation of the above three fragments is carried out in a single step.

This process makes it possible to obtain Lesopitron in very high yields and improves the synthesis from an industrial point of view.

Compound I may be prepared, according to the invention, by reacting in a suitable solvent 2-(1-piperazinyl)pyrimidine (II), 4-chloropyrazole (IV) and the carbon chain of general formula (III)

in which X and Y, which may be identical or different, each represent a suitable leaving group. X and Y represent, independently of each other, a halogen chosen from iodine, bromine or chlorine or a mesyloxy or tosyloxy group.

X and Y are preferably identical.

The reaction is carried out in a suitable solvent, for example a polar aprotic solvent such as dimethylformamide or dimethyl sulphoxide, an alcohol such as isopropanol or tert-butanol or an aromatic hydrocarbon such as toluene or xylene.

The reaction occurs in the presence of an appropriate base, which may be organic or inorganic, preferably inorganic such as an alkali metal carbonate.

The reaction temperature is between 80° C. and 180° C. and the pressure is preferably between $1.013 \times 10^5$ and $5.065 \times 10^5$ bars (1 atm and 5 atm). The reaction may be carried out without a catalyst or in the presence of one or more phase transfer agent(s), such as tetrabutyl-ammonium salts. The reaction time is advantageously between 1 and 24 hours.

By carrying out the procedure according to the invention, compound I is obtained in pure form and in very high yields. In addition, the process according the invention substantially simplifies the perfecting of the industrial process, resulting in a saving in time, energy and products necessary for the reaction.

Other characteristics will appear in the light of the example below.

EXAMPLE

Preparation of 2-{4- [4- (4-chloro-1-pyrazolyl)-butyl]-1-piperazinyl}pyrimidine.

To a mixture of 2- (1-piperazinyl)pyrimidine (32.8 g; 0.2 mol), 1,4-dibromobutane (47.5 g; 0.22 mol) and $K_2CO_3$ (69 g; 0.5 tool) in 400 ml of dimethylformamide is added 4-chloropyrazole (20.5 g; 0.2 mol), and the mixture is held at the reflux for 17 hours. The reaction mixture is filtered hot and evaporated to dryness. The residue is dissolved in HCl, washed with $CHCl_3$, rendered alkaline with dilute NaOH and extracted in basic medium with $CHCl_3$. The organic phase is then dried and subsequently evaporated to dryness, and 61 g (95%) of 2-{4-[4-(4-chloro-1-pyrazolyl)butyl]-1-piperazinyl}pyrimidine are obtained.

Spectroscopic data:

IR (film); 2843, 1586, 1547, 1358, 983 $cm^{-1}$.

$^1H$ NMR ($\delta$, $CDCl_3$): 8.25 (d, 2H, J=4.7 Hz); 7.39 (s, 1H); 7.35 (s, 1H); 6.44 (t, 1H, J=4.7 Hz); 4.0 (t, 2H, J=6.8 Hz); 3.80 (m, 4H); 2.43 (m, 6H); 1.90 (m, 2H) 1.52 (m, 2H).

According to the process of the invention, the three starting compounds of formulae II, III and IV are preferably used in approximately equimolecular proportions.

Furthermore, if a base is added in the reaction medium, it should be used in a molecular ratio base/pyrimidinylpiperazine of formula II comprised between 2 and 3.

We claim:

1. Process for the preparation of a compound of formula I:

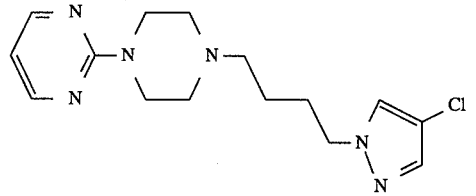

comprising reacting about equimolar amounts of 2-(1-piperazinyl)pyrimidine, 4-chloropyrazole and the carbon chain of formula (III):

 (III)

in which X and Y are independently a suitable leaving group, in a single step in a suitable solvent.

2. Process according to claim 1 characterized in that X and Y, which may be identical or different, represent a halogen chosen from iodine, bromine or chlorine, a mesyloxy group or a tosyloxy group.

3. Process according to claim 1 characterized in that X and Y are identical.

4. Process according to claim 1 characterized in that the suitable solvent is a polar aprotic solvent, an alcohol or an aromatic hydrocarbon.

5. Process according to claim 4 characterized in that the solvent is chosen from the group consisting of dimethylformamide, dimethyl sulphoxide, isopropanol, tert-butanol, toluene and xylene.

6. Process according to claim 1 characterized in that the reaction is carried out in the presence of an organic or inorganic base.

7. Process according to claim 1 characterized in that the reaction temperature is between 80° C. and 180° C.

8. Process according to claim 1 characterized in that the reaction pressure is between $1.013 \times 10^5$ and $5.065 \times 10^5$ bars (1 and 5 atm).

9. Process according to claim 1 characterized in that the reaction is carried out in the presence of one or more phase transfer agents.

10. Process according to claim 1 characterized in that the reaction time is between 1 and 24 hours.

* * * * *